(12) United States Patent
Larter et al.

(10) Patent No.: US 8,336,370 B2
(45) Date of Patent: Dec. 25, 2012

(54) METHOD FOR MEASUREMENT OF CRUDE OIL AND BITUMEN DEAD OIL VISCOSITY AND DENSITY

(75) Inventors: Stephen Richard Larter, Calgary (CA); Barry Bennett, Calgary (CA); Lloyd Ross Snowdon, Calgary (CA); Chunqing (Dennis) Jiang, Calgary (CA); Jennifer Jane Adams, Houston, TX (US); Ian Donald Gates, Calgary (CA); Kimberley Jane Noke, Calgary (CA)

(73) Assignee: Gushor Inc., Calgary (CA)

( * ) Notice: Subject to any disclaimer, the term of this patent is extended or adjusted under 35 U.S.C. 154(b) by 303 days.

(21) Appl. No.: 12/673,768

(22) PCT Filed: Aug. 5, 2008

(86) PCT No.: PCT/CA2008/001428
§ 371 (c)(1),
(2), (4) Date: Jun. 16, 2010

(87) PCT Pub. No.: WO2009/023953
PCT Pub. Date: Feb. 26, 2009

(65) Prior Publication Data
US 2011/0056271 A1    Mar. 10, 2011

(30) Foreign Application Priority Data
Aug. 17, 2007 (CA) .................................... 2597809

(51) Int. Cl.
*G01N 11/00* (2006.01)
*G01N 33/26* (2006.01)

(52) U.S. Cl. ................................ 73/54.01; 73/53.05
(58) Field of Classification Search .............. 73/54.01, 73/32 R, 54.02, 54.12, 54.17, 61.43, 61.52, 73/61.41, 61.71, 433, 53.01, 53.05; 137/92
See application file for complete search history.

(56) References Cited

U.S. PATENT DOCUMENTS 7,603,889 B2 * 10/2009 Cypes et al. ............... 73/64.53
2005/0269244 A1 * 12/2005 Zare ............................. 208/14

OTHER PUBLICATIONS

International Search Report from related International Application No. PCT/CA2008/001428 mailed Nov. 14, 2008, 2 pages.
International Preliminary Report on Patentability from related International Application No. PCT/CA2008/001428 mailed Mar. 4, 2010, 6 pages.

(Continued)

*Primary Examiner* — Helen C. Kwok
(74) *Attorney, Agent, or Firm* — Fish & Richardson P.C.

(57) ABSTRACT

Techniques for determining viscosity of oil in a sample include extracting the oil from the sample using a volatile polar first solvent; using a portion of the extracted oil to determine a concentration factor of oil in the sample; determining a dry weight of the extracted oil using the concentration factor; adding a second solvent to a remaining portion of the extract, where the second solvent is less volatile than the first solvent; removing the first solvent from the remaining portion of the extract; taking a series of sub-samples from the remaining portion of the extract and sequentially removing different amounts of the second solvent from each sub-sample; measuring solvent concentrations and viscosity values of the solvent-oil mixtures of each sub-sample; and based on the measured solvent concentrations and viscosity values of each sub-sample, determining the second-solvent-free viscosity of the oil in the sample.

27 Claims, 2 Drawing Sheets

OTHER PUBLICATIONS

Bryan, J. et al., "Viscosity determination of heavy oil and bitumen using NMR relaxometry", *J. Can Petrol. Tech.*, 2003, vol. 42, No. 7, pp. 29-34.

Wallace, D., et al., "A Correlation for Correcting the Viscosity of Solvent-Extracted Bitumen to a Solvent-Free-Basis", *Aostra J. Res.*, 1987, vol. 3, pp. 239-248.

* cited by examiner

METHOD FOR MEASUREMENT OF CRUDE OIL AND BITUMEN DEAD OIL VISCOSITY AND DENSITY

TECHNICAL FIELD

This invention relates to determining a value of a property of oil extracted from a sample.

BACKGROUND

The bulk of the world's liquid petroleum resources are located in heavy oil and oil sand reservoirs. While some of this resource can be recovered by highly geotolerant recovery processes such as mining, these procedures are typically only economic for shallow resources, are very costly, produce high carbon dioxide emissions, use large volumes of water, and incur other environmental penalties. Most of the world's heavy oil and bitumen resource is buried too deeply to mine and so in situ recovery methods predominate. Conventional in situ recovery of viscous and poor quality oils currently relies on either high pressure primary production, as in cold heavy oil production, or thermal and/or solvent-based methods to mobilize the oil by reducing its viscosity.

A defining characteristic of heavy oil and bitumen reservoirs is the significant variation of oil composition and thus fluid properties, such as oil viscosity, that is observed both vertically and laterally throughout the reservoirs. As stated in Darcy's law, the oil phase flow rate in the reservoir does not depend entirely on the permeability, but rather is directly proportional to the oil phase mobility; that is, the quotient of the oil phase effective permeability and its viscosity. In heavy oil and bitumen reservoirs, the variability of the oil phase viscosity can be substantially larger than the variation in effective permeability. Therefore, a controlling factor on production, especially by methods relying on gravity drainage, can be the oil phase viscosity.

Fluid properties commonly vary by orders of magnitude across the thickness of a reservoir, or laterally over the distance of a single horizontal production well. These substantial variations are often not taken into account (e.g., oil phase viscosity is assumed constant throughout the reservoir) when designing the operating strategy or well placement for recovery processes, even though these variations can have significant effects on production. The poor recoveries and prediction of production targets seen in many current thermal operations may be partly related to disregarding the natural variation in oil quality in heavy oil and bitumen reservoirs when designing and optimizing production strategies. In highly compositionally graded heavy oil and bitumen reservoirs, proper consideration of fluid property variations, in addition to comprehensive characterization of reservoir properties, can facilitate geotailored design of recovery methods, including well placement and optimization production strategies for each reservoir to lower operational costs and improve recovery of these viscous oils.

Thus, the incorporation of oil and bitumen viscosity variations into production planning is now being used by some in many areas of the world. The need for high resolution viscosity profiles of bitumens and heavy oils in situ has correspondingly increased.

There are several methods for recovering bitumen and oils from core samples for direct viscosity measurement with a viscosimeter, viscometer or rheometer. These methods typically involve core sample centrifugation or compaction, or displacement of the oil with an immiscible viscous fluid (mechanical recovery techniques). For samples of low viscosity, these methods can be useful. However, where the reservoir is of low permeability and/or the bitumen sample is of very high viscosity, and/or the bitumen or oil saturation of the pore space is very low and/or the core is sufficiently lithified to inhibit significant compaction, these mechanical recovery procedures are not effective. In addition, if the core sample is too small (e.g., side wall core samples) to yield sufficient bitumen to directly measure viscosity, alternative methods are required to characterize the core-hosted oil. For instance, mechanical recovery is typically ineffective for Canadian bitumen-containing carbonate reservoirs of the Devonian Grosmont Formation.

Another method for recovering oil or bitumen for analysis is the use of solvent extraction. However, since a solvent dramatically lowers the viscosity of a bitumen sample, no method has been reported which can successfully recover an accurate dead oil bitumen viscosity from analysis of solvent-containing oils. Dead oil refers to a produced oil sample where all or substantially all of the solution gas has exsolved and added solvent has been removed and the sample is at standard atmospheric pressure (1 atm) and temperature (15° C.). Prior methods of using solvent to measure viscosity of oil or bitumen were unsuccessful largely because the solvent was not completely removed prior to viscometry, or the process of solvent removal also removed volatile components in the bitumen, thus affecting the apparent dead oil viscosity. As a result, the viscosity measurement of solvent-extracted oil is generally inaccurate.

Similar problems occur for measuring density of solvent-extracted oil and such measurements are also generally inaccurate. There is therefore a need for an accurate method to measure the true dead oil bitumen viscosity and density and other properties for bitumen-containing reservoirs. There is also a need to accurately measure true viscosity and density of solvent-free oils collected by solvent-extraction.

SUMMARY

The present invention is directed to a rapid, accurate method to determine the value of a property, e.g., viscosity or density, of oil extracted from reservoirs, and in particular bitumen. The present method can be used to measure the viscosity and density of solvent-extracted oils to estimate true dead oil viscosity and density (i.e., equivalent to oil unaltered by solvent). The invention will be described with respect to viscosity measurements, but it is understood that it also applies to other property of oil as well, for example, density measurements. It is also understood that the fluid determined may be any material including one or more of petroleum, hydrocarbons or polymers that are extractable using solvents.

The process allows for an accurate determination of the solvent-free (unaltered) viscosity by using a mixture of bitumen, crude oil or other fluid containing solvent. The process includes extracting oil from a sample using a polar volatile solvent; adding a second solvent less volatile than the first solvent; sequentially and partially removing the second solvent from a series of samples of the bitumen extract; analyzing the resulting suite of samples for viscosity, and extrapolating the viscosity data to zero solvent content to determine the viscosity of the solvent-free, unaltered oil in the core or other reservoir sample. By using selected solvents and methods such as gas chromatography or gas chromatography mass spectrometry (GCMS), the present method accurately estimates solvent-free viscosity of bitumen that has been solvent extracted from core. Solvent contents can also be determined using other methods including spectroscopic methods such as infrared or UV/visible spectroscopy. The second solvent can be selected to prevent light end loss from the oil during removal of the extraction solvent and to facilitate the complete removal of the extraction solvent.

The invention can be implemented to realize one or more of the following advantages. By using the process described, viscosity of oil can be accurately determined for samples of viscosity up to $15 \times 10^6$ cP or greater at a temperature of 20° C. Viscosity can be accurately measured on small samples of less than 30 g of core or 5 g of a sidewall core sample. The viscosity can be measured on low oil saturation reservoir samples of less than 8 wt % oil and low porosity samples with less than 20 vol % porosity. It is also possible to measure viscosity on carbonate core unsuitable for mechanical extraction of oil. The viscosity of dead oil can be measured with accuracies within a few % of the true value for the viscous oils typically found in intractable bitumen containing samples. Other properties of oil (including bitumen), for example, density can similarly be measured in such traditionally intractable samples as well.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

A solvent extraction process for recovering immobile oil at ambient conditions from core samples for the purposes of estimating a property of the oil, e.g., dead oil viscosity, is described. Although the description focuses on bitumen (referred to herein at times simply as oil), it will be clear to a skilled person that the method can be used for other crude oils or any fluids containing solvent, or other viscous organic fluid in other technological applications, with appropriate selection of solvents.

By carefully selecting solvents and solvent mixtures, the method can minimize loss of volatile components during partial removal of the solvent. Further, the specific selection of the solvents in combination with the use of standard methods, such as gas chromatography or gas chromatography mass spectrometry, allow for accurate solvent contents to be assessed. Accurate estimation of the solvent content can allow the determination of accurate projected solvent-free viscosity of the bitumen or heavy oil.

Figure 1:
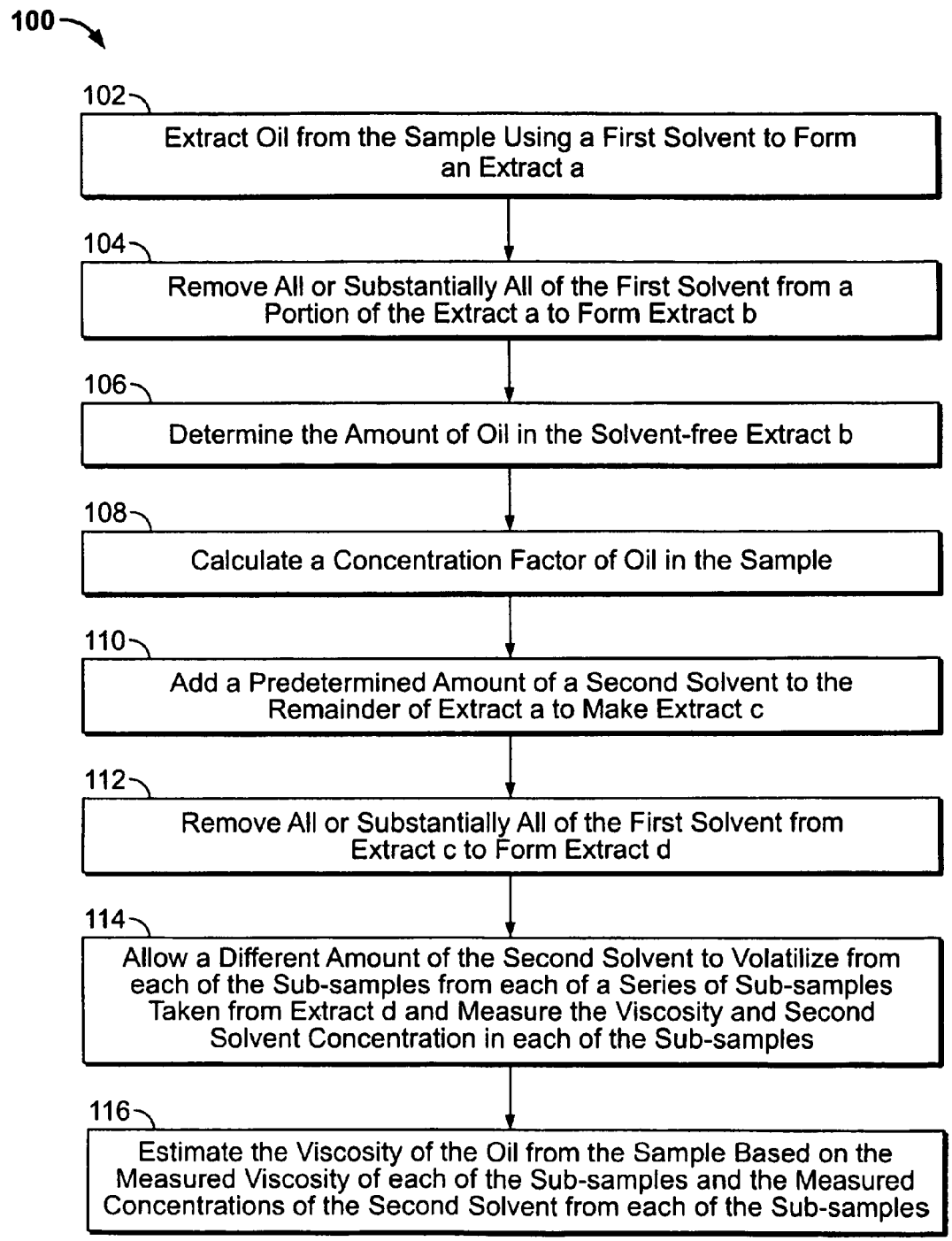
FIG. 1 is a flowchart showing an example process for estimating viscosity of oil extracted from a sample.

FIG. 1 shows an example process (100) for measuring the viscosity of oil in a sample. In some implementations, the sample can be a core sample, drill cuttings sample or other sample extracted from a reservoir using any convenient technique. Oil is extracted from the sample using a first solvent to form a first extract (extract a) (Step 102). The first solvent can be a polar volatile solvent having a much lower boiling point than a majority (i.e., approximately greater than 50%) of the oil in the sample. Preferably, the boiling point is lower than about 80% or more of the oil in the sample.

All or substantially all of the first solvent is removed from a portion of the first extract (Step 104). This portion is referred to as extract b. In some implementations, the portion is approximately 1/10 of extract a. The amount of oil in the solvent-free extract b is determined (Step 106). Based on the amount of oil in extract b, a concentration factor of oil in the sample, i.e., extract a, can be calculated (Step 108). A predetermined amount of a second solvent is added to the remainder of extract a to make extract c (Step 110). In some implementations, the predetermined amount of the second solvent is such that the second solvent is added to make extract c at a concentration of the second solvent under approximately 10% by weight of the mixture. The second solvent is a less volatile solvent than the first solvent and can have a lower boiling point than a majority of the oil in the sample, e.g., a lower boiling point than approximately 50% of more of the oil, and preferably a boiling point lower than 80% or more of the oil. The second solvent can be selected to prevent light end loss from the oil during removal of the extraction solvent (i.e., the first, more volatile, solvent) and to facilitate the complete removal of the extraction solvent.

All or substantially all of the first solvent is removed from extract c, e.g., by volatilization, but the second solvent is retained, to form extract d (Step 112). A series of sub-samples are taken from the extract d and sequentially, a different amount of the second solvent is allowed to volatilize from each of the sub-samples. The viscosity and second solvent concentration in each of the sub-samples is measured (Step 114). Based on the measured viscosity of each of the sub-samples and the measured concentrations of the second solvent from each of the sub-samples, the viscosity of the oil from the core sample can be estimated (Step 116).

The process 100 can be implemented with a small volume of reservoir sample. For example, a sample of less than 30 grams (g) can be used to obtain more than 0.5 g of bitumen for a viscosity measurement. In some implementations, the first solvent is dichloromethane (DCM), although other polar volatile solvents can be used. In some implementations, the second solvent is toluene, although other volatile solvents with a lower boiling point than a major amount of the oil, and less volatile than the first solvent, can be used. Preferably the second solvent has an excellent solubility for heavy oil and bitumen to promote the removal of the first solvent, but to prevent light end loss from the bitumen during removal of the extraction solvent.

Although the end result sought to be achieved is removal of all of the second solvent from the sample, such that viscosity of the oil can be measured, if all of the second solvent was actually removed, some of the light ends of the oil would also be removed. Removal of some of the light ends of the oil can significantly impact the viscosity of the remaining oil, therefore providing an inaccurate viscosity measurement for the sample. Accordingly, by using the series of samples with different amounts of the second solvent removed, the effective viscosity with all of the second solvent removed can be estimated. That is, by selectively removing residual toluene (an example second solvent) by evaporation, a series of bitumen-solvent mixtures with different toluene contents can be obtained, on each of which viscosity can be measured and the solvent contents determined analytically. The process 100 can also be applied with other combinations of solvents of different volatility or with mixtures of more volatile solvents for the first solvent and mixtures of less volatile solvents for the second solvent.

Once the solvent content of the sample is assessed, accurate estimation of the viscosity of the solvent-extracted oil can be determined, for example, by applying engineering mixing rules or by empirical plots of viscosity versus solvent content using a variety of non-linear curve fitting techniques. For example, one theoretically-based relationship is the logarithmic binary mixing rule for viscosity:

$$\log \mu_{mix} = x_b \log \mu_b + x_n \log \mu_n + x_b x_n d$$

wherein x is mole fraction of the component oil, μ is viscosity, mix represents mixture, n denotes oil n, b denotes oil b, and d is an interaction factor typically assumed to be zero. Other forms of the mixing rule can be volumetrically-based or mass-based viscosity rules.

At low solvent concentrations, such as below 10% by weight solvent, using such mixing rules or empirical exponential fits of solvent content and bitumen solvent viscosity plots, solvent-free bitumen viscosity can be estimated accurately by extrapolation of the viscosity-solvent content trend to the point of zero solvent content.

The following is an illustrative example of the measurement of viscosity for bitumen in a tar sand sample.

EXAMPLE 1

For a tar sand sample with approximately 10 wt % bitumen saturation, 6 to 10 g of core can provide a sufficient bitumen material. In this example, the viscometer/rheometer required approximately 0.5 g or 0.5 mL of fluid (or extracted equivalent). The example involved the following steps.

Extraction:
1) Extracted approximately 10-20 g of crushed core material with a volatile polar solvent, dichloromethane (DCM). Other volatile polar solvents (about 250 mL) can be used.
2) Removed solvent to a minimum volume of 10 mL via Buchi (rotary evaporator).
3) Transferred extract to a measuring cylinder and removed an aliquot (1/10 by volume).
4) The aliquot was transferred to a pre-weighed aluminum weighing dish (about 5 cm ID, 20 mL volume) to let solvent evaporate. Solvent can also be removed using a stream of nitrogen gas, or leaving the extract in the fume hood at room temperature.
5) Following complete (or almost complete) removal of solvent, weighed the total extract and determined the concentration factor of bitumen.

Solvent Addition and Buchi Rotary Evaporation:
6) For the remaining dissolved extract aliquot (9/10 of material at step 3 above), calculated the apparent dry weight of bitumen in the sample using the concentration factor determined at step 5.
7) Determined the amount of toluene (i.e. second, less volatile solvent) required to be added to this to make up 10% of the weight in the final extract plus toluene mixture. The 10% toluene addition is done because during Buchi rotary evaporation, the final loss of DCM from the system will also occur with some toluene loss (up to 25% of the toluene). However, toluene removal is notoriously difficult and time consuming, so there will always be residual toluene keeping the sample light ends in solution.

Viscometer Procedure:
8) Set the viscometer temperature to about 20° C.
9) Transferred 0.50 mL Extract plus Toluene using a syringe into the viscometer cell.
10) Measured viscosity at 20° C.
11) Opened the viscometer cell and used a pipette tip to remove a tiny scraping of the extract+toluene mixture that was inserted into a GC-MS auto-sampler vial containing ~½ mL DCM. Left the viscometer cell open to the atmosphere and set the temperature to 35° C. For very high viscosity samples, the sample container may have to be heated to 50° C. The temperature ramp rate is set by the instrument. Once the temperature reached 35° C., it was held for 3-5 minutes, ensuring adequate air circulation over both the spindle and sample cell to remove a portion of the residual toluene. Cooled the sample down to 20° C. using standard techniques.
12) Attached the cell back onto the viscometer (when the temperature was about 22° C.) and measured the extract-toluene viscosity at 20° C.
13) Opened the viscometer cell and with a new pipette tip, took a scraping of extract plus toluene into a second GC-MS vial.
14) Repeated the temperature cycle (20 to 35° C. open viscometer cell, hold, and back to 20° C. (connect viscometer cell)). Toluene was gradually evaporated from the sample, and therefore successive sample collections yielded a gradual reduction in toluene response (GC-MS, GC-FID, etc.) relative to the response due to the extract with a corresponding set of viscosity values for each solvent oil mixture.
15) Up to 5 or 6 samples with different toluene contents were collected in this way for preparation for GC-based solvent content determination.
16) Following removal of the final sample, the temperature can be run through a suite of temperatures or the bitumen can be potentially recovered from the viscometer cell for high temperature viscosity determination or other analysis.

To enable more rapid generation of a suite of solvent content and viscosity measurements, modifications to the viscometer can assist the method. For example, adding a gas flushing system or vacuum vapor extraction system to remove solvent more quickly from the cell after an individual viscosity measurement has been taken can assist the process.

The samples of bitumen plus solvent mixtures can be characterized by gas chromatography, or gas chromatography mass spectrometry, to determine second solvent (e.g., toluene) content. This can be done either by direct determination of solvent concentration using internal or external standard methodologies, or by simply using peak height ratios of solvent peak to bitumen chromatogram maximum hump height. Infrared (IR) or Ultraviolet (UV) spectroscopy can also be used. The solvent-free viscosity determination can be obtained by using an appropriate correlation or mixing algorithm and/or using regression, with either an exponential or other function, to fit to a minimum of three second solvent (e.g., toluene) concentrations by weight of total bitumen versus viscosity. The solvent-free bitumen viscosity estimate values can be obtained by the extrapolated viscosity obtained at 0% second solvent using a fitting function appropriate for the bitumen-solvent system in use. For example, a least squares fit can be an exponential function is often adequate to establish an appropriately accurate zero-solvent content viscosity value (i.e., true dead oil viscosity).

Figure 2:
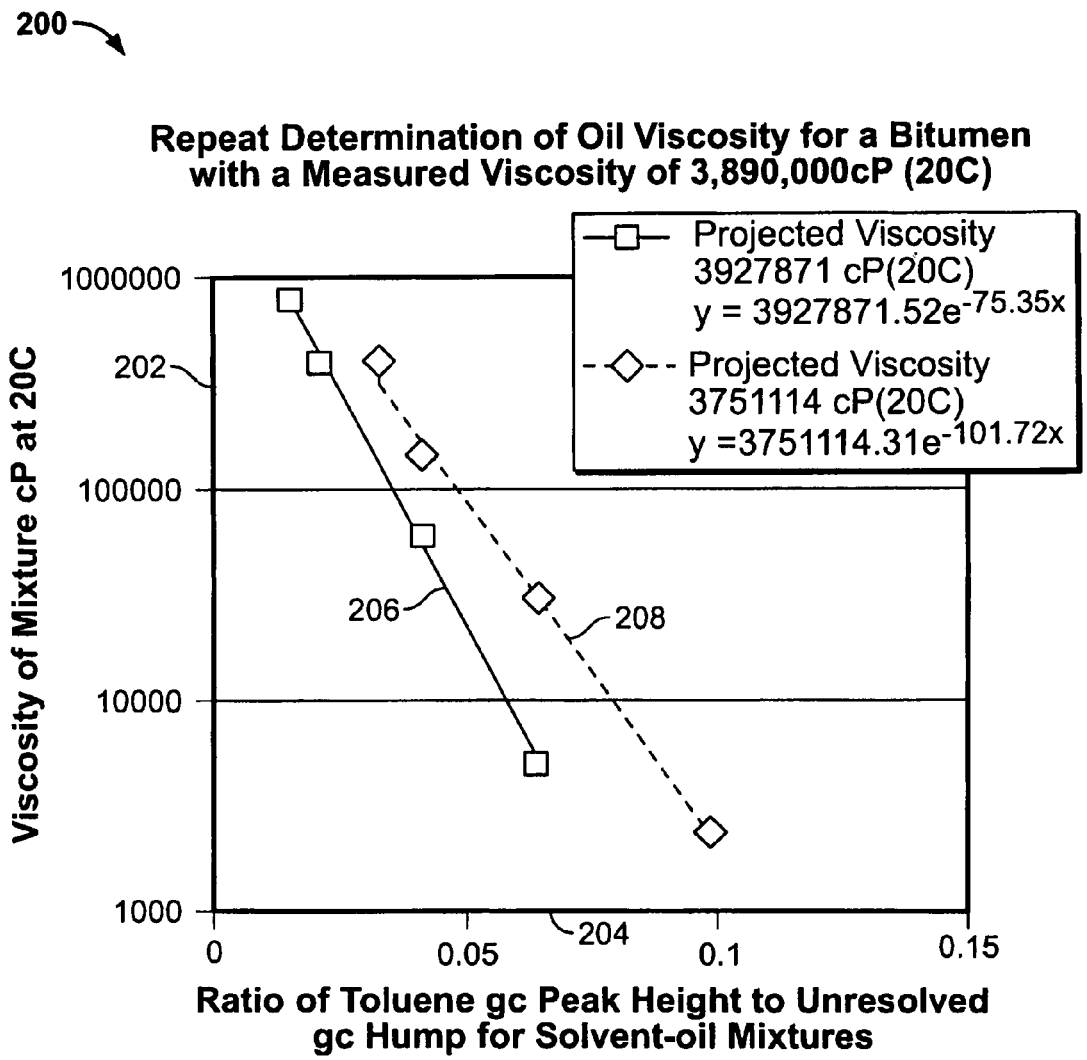
FIG. 2 is an example plot showing results from duplicate analyses of a bitumen sample for viscosity using the example process shown in FIG. 1.

FIG. 2 is a plot 200 showing viscosity of the mixture on the vertical axis 202 versus the ratio of the second solvent (e.g., toluene) gas chromatogram (gc) peak height to the height of the unresolved gc hump for solvent-oil mixtures on the horizontal axis 204. The plot 200 shows the viscosity of the bitumen-second solvent mixture (second solvent in this example is toluene) plotted on a log scale versus the relative amount of second solvent in the mixture estimated by gas chromatography of the solvent-bitumen mixture. Also shown for comparison are the projected viscosity values at zero solvent content for the two sets of analyses (see 206 and 208) from a fitting algorithm (3,927,871 cP and 3,751,114 cP at 20° C.), which are very close to the actual bitumen viscosity measured on a different mechanically recovered equivalent bitumen sample (3,890,000 cP at 20 C). The plot shows a typical result for a single sample. In this representative case, two operators independently performed the process 100 to estimate the viscosity of bitumen extracted from a Canadian tar sand sample, with a known bitumen viscosity of 3,890,000 cP at 20° C. The solvent content was estimated as a ratio of solvent (toluene peak height) to the maximum peak height of the hump in the gas chromatogram of the bitumen. Using the present method and the logarithmic or exponential mixing rule, the two operators estimated a bitumen viscosity of 3,751,114 cP (line 208) and 3,927,871 cP (line 206), both well within 10% of the measured value on mechanically extracted bitumen from an equivalent core sample.

In other implementations, other properties of the oil in the sample can be estimated by using similar techniques. For example, the density of the oil in a sample can be estimated, rather than the viscosity. In this implementation, the density is measured for each of the sub-samples of the solvent-bitumen mixture, algorithmic fits of density versus solvent content for a range of solvent-bitumen mixtures can be used to determine densities of solvent free oil or bitumen from solvent containing mixtures. This process can be used to determine density, and therefore API gravity, of solvent-free bitumen or oils from solvent extracted bitumen or oils.

As discussed, the process 100 can be used to determine other properties of oil or bitumen contained within a sample. Viscosity and density are two such examples. However, other examples include other physical properties such as interfacial tension, or bulk chemical properties such as total acid number. The property of the solvent containing mixture is determined along with the second solvent content, and the property at zero solvent content can be determined by extrapolation using an appropriate curve fitting algorithm of property mixing rule.

In other implementations, a two-variable algorithmic fit can be obtained for the sub-samples of the solvent-oil or solvent-bitumen mixture versus solvent content and temperature to determine viscosity or density of solvent-free oil or bitumen. Higher order, multiple parameter fits can be done to extract the properties of solvent-free oil or bitumen.

In other implementation, the algorithmic fit of the properties of the sub-samples of the solvent-oil or solvent-bitumen versus solvent content, temperature, and other parameters can be used to obtain a property at a specified solvent content and temperature.

The embodiments of the present invention described above are examples of the present invention and not limiting. A person skilled in the art understands that variations and modifications of the method can be done without departing from the invention. Such variations and modifications are contemplated by the inventors and fall within the scope of the present invention.

The invention claimed is:

1. A method for determining viscosity of oil in a sample, comprising:
    extracting the oil from the sample using a volatile polar first solvent;
    using a portion of the extracted oil to determine a concentration factor of oil in the sample;
    determining a dry weight of the extracted oil using the concentration factor;
    adding a second solvent to a remaining portion of the extract, the second solvent less volatile than the first solvent;
    removing the first solvent from the remaining portion of the extract;
    taking a series of sub-samples from the remaining portion of the extract and sequentially removing different amounts of the second solvent from each sub-sample;
    measuring solvent concentrations and viscosity values of the solvent-oil mixtures of each sub-sample; and
    based on the measured solvent concentrations and viscosity values of each sub-sample, determining the second-solvent-free viscosity of the oil in the sample.

2. The method of claim 1, wherein determining the second-solvent-free viscosity of the oil in the sample comprises using a fitting algorithm.

3. The method of claim 1, wherein the first solvent has a lower boiling point than at least 50% of the oil contained in the sample.

4. The method of claim 1, wherein the second solvent has a lower boiling point than a least 50% of the oil contained in the sample.

5. The method of claim 1, wherein the second solvent is selected to prevent light end loss from the oil during removal of the first solvent and to facilitate the removal of the first solvent.

6. A method for determining viscosity of oil in a sample comprising:
    extracting oil from the sample using a first solvent to form an extract a, wherein the first solvent is a polar volatile solvent having a lower boiling point than at least 50% of the oil in the sample;
    removing substantially all of the first solvent from a small portion of the extract a to form an extract b;
    determining an amount of oil in the solvent-free extract b;
    adding a predetermined amount of a second solvent to the remainder of extract a to make an extract c, wherein the second solvent is a less volatile solvent than the first solvent and has a lower boiling point than at least 50% of the oil in the sample;
    removing, from the extract c, substantially all of the first solvent while retaining the second solvent to form an extract d;
    allowing a different amount of the second solvent to volatilize from each of a series of sub-samples taken from the extract d;
    measuring a viscosity and second solvent concentration in each of the sub-samples; and
    based on the measured viscosity of each of the sub-samples and the measured solvent concentrations of the second solvent from each of the sub-samples, determining the viscosity of the oil from the sample, the viscosity representing the viscosity of the oil free of the second solvent.

7. The method of claim 6, wherein the first solvent is dichloromethane (DCM).

8. The method of claim 6, wherein the second solvent is toluene.

9. The method of claim 6, wherein the solvent concentration is determined using gas chromatography or gas chromatography-mass spectrometry.

10. The method of claim 6, wherein determining the viscosity of the second-solvent-free oil from the sample comprises combining respective viscosity values measured on each of the extracts using viscosity mixing rules or non linear fitting algorithms to derive the second-solvent-free oil viscosity.

11. The method of claim 6, wherein the second solvent is selected to prevent light end loss from the oil during removal of the first solvent and to facilitate the removal of the first solvent.

12. A method for measuring density of oil in a sample, comprising:
- extracting the oil from the sample using a volatile polar first solvent;
- using a portion of the extracted oil to determine a concentration factor of oil in the sample;
- calculating a dry weight of the extracted oil using the concentration factor;
- adding a second solvent to a remaining portion of the extract, the second solvent less volatile than the first solvent;
- removing the first solvent from the remaining portion of the extract;
- sequentially removing different amounts of the second solvent from each of a series of sub-samples taken from the remaining portion of the extract;
- measuring solvent concentrations and density values of the solvent-oil mixtures of each sub-sample; and
- based on the measured solvent concentrations and density values of each sub-sample, determining a second-solvent-free density of the oil in the sample.

13. The method of claim 12, further comprising determining a second-solvent-free API gravity of the oil in the sample based on the determined second-solvent-free density of the oil.

14. The method of claim 12, wherein determining the second-solvent-free density of the oil in the sample comprises using a fitting algorithm.

15. The method of claim 12, wherein the first solvent has a lower boiling point than at least 50% of the oil contained in the sample.

16. The method of claim 12, wherein the second solvent has a lower boiling point than at least 50% of the oil contained in the sample.

17. The method of claim 12, wherein the second solvent is selected to prevent light end loss from the oil during removal of the first solvent and to facilitate the removal of the first solvent.

18. A method for determining a value of a property of oil in a sample, comprising:
- extracting the oil from the sample using a volatile polar first solvent;
- using a portion of the extracted oil to determine a concentration factor of oil in the sample;
- determining a dry weight of the extracted oil using the concentration factor;
- adding a second solvent to a remaining portion of the extract, the second solvent less volatile than the first solvent;
- removing the first solvent from the remaining portion of the extract;
- taking a series of sub-samples from the remaining portion of the extract and sequentially removing different amounts of the second solvent from each sub-sample;
- measuring solvent concentrations and values of the property of the solvent-oil mixtures of each sub-sample; and
- based on the measured solvent concentrations and property values of each sub-sample, determining a second-solvent-free value of the property for the oil in the sample.

19. The method of claim 18, wherein the property is a physical property of the oil.

20. The method of claim 19, wherein the physical property is a viscosity of the oil.

21. The method of claim 19, wherein the physical property is a density of the oil.

22. The method of claim 19, wherein the physical property is an interfacial tension of the oil.

23. The method of claim 18, wherein the property is a bulk chemical property of the oil.

24. The method of claim 23, wherein the bulk chemical property is a total acid number of the oil.

25. The method of claim 18, wherein the first solvent is dichloromethane (DCM) and the second solvent is toluene.

26. The method of claim 18, wherein determining the property of the second-solvent-free oil from the sample comprises combining the property values measured on each of the extracts using mixing rules or non linear fitting algorithms to derive the second-solvent-free oil value of the property.

27. The method of claim 18, wherein the second solvent is selected to prevent light end loss from the oil during removal of the first solvent and to facilitate the removal of the first solvent.

* * * * *

UNITED STATES PATENT AND TRADEMARK OFFICE
CERTIFICATE OF CORRECTION

PATENT NO. : 8,336,370 B2
APPLICATION NO. : 12/673768
DATED : December 25, 2012
INVENTOR(S) : Stephen Richard Larter et al.

It is certified that error appears in the above-identified patent and that said Letters Patent is hereby corrected as shown below:

In the Claims

Column 8, Line 18, in claim 4, delete "a least" and insert -- at least --, therefor.

Signed and Sealed this
Fourteenth Day of May, 2013

Teresa Stanek Rea
*Acting Director of the United States Patent and Trademark Office*